(12) United States Patent
Trieu

(10) Patent No.: US 8,414,619 B2
(45) Date of Patent: *Apr. 9, 2013

(54) VERTEBRAL RODS AND METHODS OF USE

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 197 days.

This patent is subject to a terminal disclaimer.

(21) Appl. No.: 12/896,966

(22) Filed: Oct. 4, 2010

(65) Prior Publication Data

US 2011/0022092 A1    Jan. 27, 2011

Related U.S. Application Data

(62) Division of application No. 11/340,973, filed on Jan. 27, 2006, now Pat. No. 7,815,663.

(51) Int. Cl.
*A61B 17/70* (2006.01)

(52) U.S. Cl.
USPC .......................... 606/254; 606/257; 606/259

(58) Field of Classification Search .......... 606/254–259, 606/264, 278
See application file for complete search history.

(56) References Cited

U.S. PATENT DOCUMENTS

| | | |
|---|---|---|
| 4,743,260 A | 5/1988 | Burton |
| 5,092,866 A | 3/1992 | Breard et al. |
| 5,180,393 A | 1/1993 | Commarmond |
| 5,282,863 A | 2/1994 | Burton |
| 5,375,823 A | 12/1994 | Navas |
| 5,415,661 A | 5/1995 | Holmes |
| 5,423,816 A | 6/1995 | Lin |
| 5,458,642 A | 10/1995 | Beer et al. |
| 5,480,401 A | 1/1996 | Navas |
| 5,540,688 A | 7/1996 | Navas |
| 5,562,737 A | 10/1996 | Graf |
| 5,584,834 A | 12/1996 | Errico et al. |
| 5,645,599 A | 7/1997 | Samani |
| 5,672,175 A | 9/1997 | Martin |
| 5,676,702 A | 10/1997 | Ratron |
| 5,702,450 A | 12/1997 | Bisserie |
| 5,704,936 A | 1/1998 | Mazel |
| 5,713,899 A | 2/1998 | Marnay et al. |

(Continued)

FOREIGN PATENT DOCUMENTS

| | | |
|---|---|---|
| DE | 43 15 757 C1 | 11/1994 |
| EP | 0 642 775 | 3/1995 |

(Continued)

OTHER PUBLICATIONS

International Search Report and Written Opinion for PCT/US2007/060966 mailed on Jun. 13, 2007.

(Continued)

*Primary Examiner* — Pedro Philogene

(57) ABSTRACT

The present application is directed to vertebral rods and methods of use. In one embodiment, the rod includes upper and lower sections that are separated by an intermediate section. The intermediate section may include one or more members, and may have a variety of configurations. An elastic member may be positioned within the intermediate section. The intermediate section and the elastic member may provide for variable resistance during movement of the upper and lower sections. In one embodiment, the resistance increases the further away the upper and lower sections move from a first orientation.

20 Claims, 9 Drawing Sheets

U.S. PATENT DOCUMENTS

| | | |
|---|---|---|
| 5,733,284 A | 3/1998 | Martin |
| 5,749,916 A | 5/1998 | Richelsoph |
| 5,836,948 A | 11/1998 | Zucherman et al. |
| 5,928,284 A | 7/1999 | Mehdizadeh |
| 5,961,516 A | 10/1999 | Graf |
| 5,993,448 A | 11/1999 | Remmler |
| 6,231,609 B1 | 5/2001 | Mehdizadeh |
| 6,241,730 B1 | 6/2001 | Alby |
| 6,248,106 B1 | 6/2001 | Ferree |
| 6,267,764 B1 | 7/2001 | Elberg |
| 6,293,949 B1 | 9/2001 | Justis et al. |
| 6,296,643 B1 | 10/2001 | Hopf et al. |
| 6,402,750 B1 | 6/2002 | Atkinson et al. |
| 6,440,169 B1 * | 8/2002 | Elberg et al. ............... 623/17.16 |
| 6,478,796 B2 | 11/2002 | Zucherman et al. |
| 6,514,256 B2 | 2/2003 | Zucherman et al. |
| 6,527,804 B1 | 3/2003 | Gauchet et al. |
| 6,527,806 B2 | 3/2003 | Ralph et al. |
| 6,540,785 B1 | 4/2003 | Gill et al. |
| 6,616,669 B2 | 9/2003 | Ogilvie et al. |
| 6,626,904 B1 | 9/2003 | Jammet et al. |
| 6,626,944 B1 | 9/2003 | Taylor |
| 6,645,207 B2 | 11/2003 | Dixon et al. |
| 6,706,044 B2 | 3/2004 | Kuslich et al. |
| 6,733,534 B2 | 5/2004 | Sherman |
| 6,743,257 B2 | 6/2004 | Castro |
| 6,761,719 B2 | 7/2004 | Justis et al. |
| 6,766,910 B1 | 7/2004 | Kelly et al. |
| 6,783,527 B2 | 8/2004 | Drewry et al. |
| 6,793,679 B2 | 9/2004 | Michelson |
| 6,796,983 B1 | 9/2004 | Zucherman et al. |
| 6,835,205 B2 | 12/2004 | Atkinson et al. |
| 6,893,466 B2 | 5/2005 | Trieu |
| 6,966,910 B2 * | 11/2005 | Ritland ............... 606/257 |
| 6,986,771 B2 | 1/2006 | Paul et al. |
| 6,989,011 B2 | 1/2006 | Paul et al. |
| 6,991,632 B2 | 1/2006 | Ritland |
| 7,018,379 B2 | 3/2006 | Drewry et al. |
| 7,029,475 B2 | 4/2006 | Panjabi |
| 7,066,957 B2 | 6/2006 | Graf |
| 7,083,621 B2 | 8/2006 | Shaolian et al. |
| 7,083,622 B2 | 8/2006 | Simonson |
| 7,125,410 B2 | 10/2006 | Freudiger |
| 7,137,985 B2 | 11/2006 | Jahng |
| 7,229,441 B2 | 6/2007 | Trieu et al. |
| 7,255,713 B2 | 8/2007 | Malek |
| 7,282,065 B2 | 10/2007 | Kirschman |
| 7,285,121 B2 | 10/2007 | Braun et al. |
| 7,291,150 B2 | 11/2007 | Graf |
| 7,297,146 B2 | 11/2007 | Braun et al. |
| 7,326,210 B2 | 2/2008 | Jahng et al. |
| 7,329,258 B2 | 2/2008 | Studer |
| 7,335,200 B2 | 2/2008 | Carli |
| 7,338,525 B2 | 3/2008 | Ferree |
| 7,361,196 B2 | 4/2008 | Fallin et al. |
| 7,377,921 B2 | 5/2008 | Studer et al. |
| 7,476,238 B2 | 1/2009 | Panjabi |
| 7,556,639 B2 | 7/2009 | Rothman et al. |
| 7,559,942 B2 | 7/2009 | Paul et al. |
| 7,578,849 B2 | 8/2009 | Trieu |
| 7,601,166 B2 | 10/2009 | Biedermann et al. |
| 7,604,653 B2 | 10/2009 | Kitchen |
| 7,604,654 B2 | 10/2009 | Fallin et al. |
| 7,815,663 B2 * | 10/2010 | Trieu ............... 606/254 |
| 7,927,358 B2 * | 4/2011 | Hudgins et al. ............... 606/262 |
| 2001/0007073 A1 | 7/2001 | Zucherman et al. |
| 2002/0120270 A1 | 8/2002 | Trieu et al. |
| 2002/0133155 A1 | 9/2002 | Ferree |
| 2003/0109880 A1 | 6/2003 | Shirado et al. |
| 2003/0114853 A1 | 6/2003 | Burgess et al. |
| 2003/0171749 A1 | 9/2003 | Le Couedic et al. |
| 2003/0191470 A1 | 10/2003 | Ritland |
| 2003/0220643 A1 | 11/2003 | Ferree |
| 2004/0002708 A1 | 1/2004 | Ritland |
| 2004/0006343 A1 | 1/2004 | Sevrain |
| 2004/0015166 A1 | 1/2004 | Gorek |
| 2004/0049189 A1 | 3/2004 | LeCouedic |
| 2004/0049190 A1 | 3/2004 | Biedermann et al. |
| 2004/0073215 A1 | 4/2004 | Carli |
| 2004/0106995 A1 | 6/2004 | Le Couedic et al. |
| 2004/0143264 A1 | 7/2004 | McAfee |
| 2004/0147928 A1 | 7/2004 | Landry et al. |
| 2004/0172024 A1 | 9/2004 | Gorek |
| 2004/0215191 A1 | 10/2004 | Kitchen |
| 2004/0215192 A1 | 10/2004 | Justis et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0243239 A1 | 12/2004 | Taylor |
| 2004/0267260 A1 | 12/2004 | Mack et al. |
| 2005/0043796 A1 | 2/2005 | Grant et al. |
| 2005/0049708 A1 | 3/2005 | Atkinson et al. |
| 2005/0055244 A1 | 3/2005 | Mullan et al. |
| 2005/0065516 A1 | 3/2005 | Jahng |
| 2005/0085814 A1 | 4/2005 | Sherman et al. |
| 2005/0085815 A1 | 4/2005 | Harms et al. |
| 2005/0113927 A1 | 5/2005 | Malek |
| 2005/0124991 A1 | 6/2005 | Jahng |
| 2005/0125063 A1 | 6/2005 | Matge et al. |
| 2005/0131407 A1 | 6/2005 | Sicvol et al. |
| 2005/0143737 A1 | 6/2005 | Pafford et al. |
| 2005/0143823 A1 | 6/2005 | Boyd et al. |
| 2005/0143827 A1 | 6/2005 | Globerman et al. |
| 2005/0149020 A1 | 7/2005 | Jahng |
| 2005/0149023 A1 | 7/2005 | Ritland |
| 2005/0154390 A1 | 7/2005 | Biedermann et al. |
| 2005/0165396 A1 | 7/2005 | Fortin |
| 2005/0171540 A1 | 8/2005 | Lim et al. |
| 2005/0171543 A1 | 8/2005 | Timm et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0182400 A1 | 8/2005 | White |
| 2005/0182401 A1 | 8/2005 | Timm et al. |
| 2005/0182409 A1 | 8/2005 | Callahan et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203518 A1 | 9/2005 | Biedermann et al. |
| 2005/0203519 A1 | 9/2005 | Harms et al. |
| 2005/0209694 A1 | 9/2005 | Loeb |
| 2005/0222569 A1 | 10/2005 | Panjabi |
| 2005/0261685 A1 | 11/2005 | Fortin |
| 2005/0261686 A1 | 11/2005 | Paul |
| 2005/0261768 A1 | 11/2005 | Trieu |
| 2005/0277922 A1 | 12/2005 | Trieu et al. |
| 2005/0277934 A1 | 12/2005 | Vardiman |
| 2005/0288670 A1 | 12/2005 | Panjabi et al. |
| 2005/0288672 A1 | 12/2005 | Ferree |
| 2006/0004367 A1 | 1/2006 | Alamin et al. |
| 2006/0009768 A1 | 1/2006 | Ritland |
| 2006/0009846 A1 | 1/2006 | Trieu et al. |
| 2006/0036240 A1 | 2/2006 | Colleran et al. |
| 2006/0041259 A1 | 2/2006 | Paul et al. |
| 2006/0064090 A1 | 3/2006 | Park |
| 2006/0084982 A1 | 4/2006 | Kim |
| 2006/0084984 A1 | 4/2006 | Kim |
| 2006/0084987 A1 | 4/2006 | Kim |
| 2006/0084991 A1 | 4/2006 | Borgstrom |
| 2006/0089645 A1 | 4/2006 | Eckman |
| 2006/0142758 A1 | 6/2006 | Petit |
| 2006/0142760 A1 | 6/2006 | McDonnell |
| 2006/0184171 A1 | 8/2006 | Biedermann et al. |
| 2006/0189985 A1 | 8/2006 | Lewis |
| 2006/0195093 A1 | 8/2006 | Jahng |
| 2006/0212033 A1 | 9/2006 | Rothman et al. |
| 2006/0229608 A1 | 10/2006 | Foster et al. |
| 2006/0229612 A1 | 10/2006 | Rothman et al. |
| 2006/0247623 A1 | 11/2006 | Anderson et al. |
| 2006/0247632 A1 | 11/2006 | Winslow et al. |
| 2006/0247637 A1 * | 11/2006 | Colleran et al. ............... 606/61 |
| 2006/0264935 A1 | 11/2006 | White |
| 2006/0264937 A1 | 11/2006 | White |
| 2006/0271048 A1 | 11/2006 | Thramann |
| 2006/0276247 A1 | 12/2006 | Martinez |
| 2006/0276790 A1 | 12/2006 | Dawson et al. |
| 2006/0282080 A1 | 12/2006 | Albert et al. |

| | | |
|---|---|---|
| 2006/0293657 A1 | 12/2006 | Hartmann |
| 2007/0005062 A1 | 1/2007 | Lange et al. |
| 2007/0016190 A1 | 1/2007 | Martinez et al. |
| 2007/0016193 A1 | 1/2007 | Ritland |
| 2007/0016200 A1 | 1/2007 | Jackson |
| 2007/0016201 A1 | 1/2007 | Freudiger |
| 2007/0043356 A1 | 2/2007 | Timm et al. |
| 2007/0049936 A1 | 3/2007 | Colleran et al. |
| 2007/0049937 A1 | 3/2007 | Matthis et al. |
| 2007/0055244 A1 | 3/2007 | Jackson |
| 2007/0055247 A1 | 3/2007 | Jahng |
| 2007/0073289 A1 | 3/2007 | Kwak et al. |
| 2007/0088359 A1 | 4/2007 | Woods et al. |
| 2007/0100341 A1 | 5/2007 | Reglos et al. |
| 2007/0118122 A1 | 5/2007 | Butler et al. |
| 2007/0123865 A1 | 5/2007 | Schlapfer et al. |
| 2007/0123871 A1 | 5/2007 | Jahng |
| 2007/0129729 A1 | 6/2007 | Petit et al. |
| 2007/0191832 A1 | 8/2007 | Trieu |
| 2007/0191846 A1 | 8/2007 | Bruneau et al. |
| 2007/0198088 A1 | 8/2007 | Biedermann |
| 2007/0213719 A1 | 9/2007 | Hudgins et al. |
| 2007/0225710 A1 | 9/2007 | Jahng et al. |
| 2007/0233064 A1 | 10/2007 | Holt |
| 2007/0270838 A1 | 11/2007 | Bruneau et al. |
| 2007/0270860 A1 | 11/2007 | Jackson |
| 2007/0276380 A1* | 11/2007 | Jahng et al. ............. 606/61 |
| 2007/0276500 A1 | 11/2007 | Zucherman et al. |
| 2007/0288008 A1 | 12/2007 | Park |
| 2007/0288093 A1 | 12/2007 | Le Couedic et al. |
| 2007/0293862 A1 | 12/2007 | Jackson |
| 2008/0021459 A1 | 1/2008 | Lim |
| 2008/0027549 A1 | 1/2008 | Kirschman |
| 2008/0033435 A1 | 2/2008 | Studer et al. |
| 2008/0039943 A1 | 2/2008 | Le Couedic |
| 2008/0045951 A1 | 2/2008 | Fanger et al. |
| 2008/0065071 A1 | 3/2008 | Park |
| 2008/0097431 A1 | 4/2008 | Vessa |
| 2008/0097434 A1 | 4/2008 | Moumene et al. |
| 2008/0140076 A1 | 6/2008 | Jackson |
| 2008/0140122 A1 | 6/2008 | Bethell |
| 2008/0147122 A1 | 6/2008 | Jackson |
| 2008/0154307 A1 | 6/2008 | Colleran et al. |
| 2008/0161854 A1 | 7/2008 | Bae et al. |
| 2008/0172091 A1 | 7/2008 | Anderson |
| 2008/0177316 A1 | 7/2008 | Bergeron et al. |
| 2008/0177317 A1 | 7/2008 | Jackson |
| 2008/0177320 A1 | 7/2008 | McBride |
| 2008/0177329 A1 | 7/2008 | Perez-Cruet et al. |
| 2008/0177331 A1 | 7/2008 | Perez-Cruet et al. |
| 2008/0183212 A1 | 7/2008 | Veldman et al. |
| 2008/0183213 A1 | 7/2008 | Veldman et al. |
| 2008/0215094 A1 | 9/2008 | Taylor |
| 2008/0221620 A1 | 9/2008 | Krause |
| 2008/0234739 A1 | 9/2008 | Hudgins et al. |
| 2008/0234744 A1 | 9/2008 | Zylber et al. |
| 2008/0255617 A1 | 10/2008 | Cho et al. |
| 2008/0262554 A1 | 10/2008 | Hayes et al. |
| 2008/0294195 A1 | 11/2008 | Egli et al. |
| 2008/0294197 A1 | 11/2008 | Egli et al. |
| 2008/0300633 A1 | 12/2008 | Jackson |
| 2008/0306450 A1 | 12/2008 | Martin |
| 2008/0306451 A1 | 12/2008 | Woehr et al. |
| 2008/0306452 A1 | 12/2008 | Crawford |
| 2008/0312694 A1 | 12/2008 | Peterman et al. |
| 2008/0319482 A1 | 12/2008 | Jackson |
| 2008/0319486 A1 | 12/2008 | Hestad et al. |
| 2009/0005817 A1 | 1/2009 | Friedrich et al. |
| 2009/0012562 A1 | 1/2009 | Hestad et al. |
| 2009/0030465 A1 | 1/2009 | Altarac et al. |
| 2009/0048631 A1 | 2/2009 | Bhatnagar et al. |
| 2009/0054932 A1 | 2/2009 | Butler et al. |
| 2009/0093819 A1 | 4/2009 | Joshi |
| 2009/0093845 A1 | 4/2009 | Hestad et al. |
| 2009/0093846 A1 | 4/2009 | Hestad |
| 2009/0099606 A1 | 4/2009 | Hestad et al. |
| 2009/0099607 A1 | 4/2009 | Fallin et al. |
| 2009/0105762 A1 | 4/2009 | Jackson |
| 2009/0112265 A1 | 4/2009 | Hudgins et al. |
| 2009/0118767 A1 | 5/2009 | Hestad et al. |
| 2009/0131981 A1 | 5/2009 | White |
| 2009/0163953 A1 | 6/2009 | Biedermann et al. |
| 2009/0163955 A1 | 6/2009 | Moumene et al. |
| 2009/0171395 A1 | 7/2009 | Jeon et al. |
| 2009/0192548 A1 | 7/2009 | Jeon et al. |
| 2009/0228043 A9 | 9/2009 | Egli et al. |
| 2009/0228044 A1 | 9/2009 | Jeon et al. |
| 2009/0228045 A1 | 9/2009 | Hayes et al. |

FOREIGN PATENT DOCUMENTS

| | | |
|---|---|---|
| EP | 1 287 794 | 3/2003 |
| FR | 2 722 980 | 2/1996 |
| FR | 2 774 581 | 8/1999 |
| FR | 2 844 180 A1 | 3/2004 |
| FR | 2 860 428 | 4/2005 |
| WO | WO 01/62190 A1 | 8/2001 |
| WO | WO 02/102259 A2 | 12/2002 |
| WO | WO 2004/089244 A2 | 10/2004 |
| WO | WO 2004/105577 A2 | 12/2004 |
| WO | WO 2005/011522 A2 | 2/2005 |
| WO | WO 2006/106246 A2 | 10/2006 |

OTHER PUBLICATIONS

Trieu, Hai H., "Intervertebral Implants and Methods of Use." Filed Jan. 27, 2006, 29 pages, U.S. Appl. No. 11/340,972.

Trieu, Hai H., "Interspinous Devices and Methods of Use." Filed Jan. 27, 2006, 31 pages, U.S. Appl. No. 11/341,200.

* cited by examiner

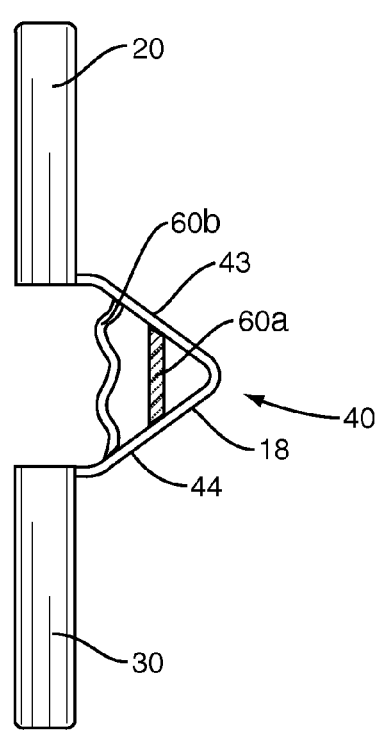
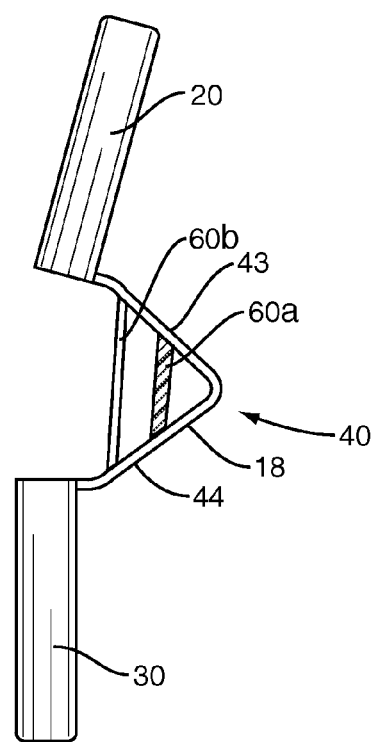
FIG. 11A     FIG. 11B
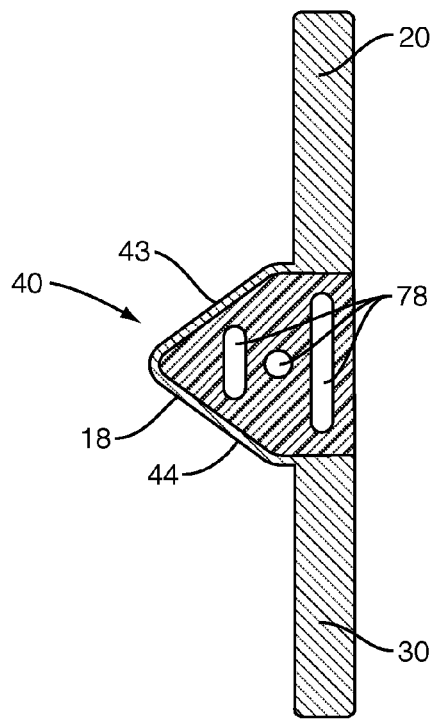
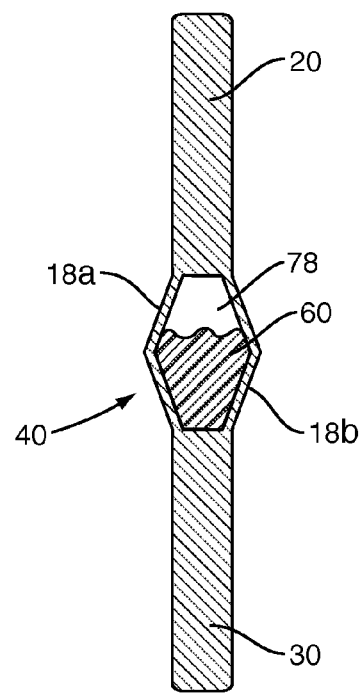
FIG. 12     FIG. 13

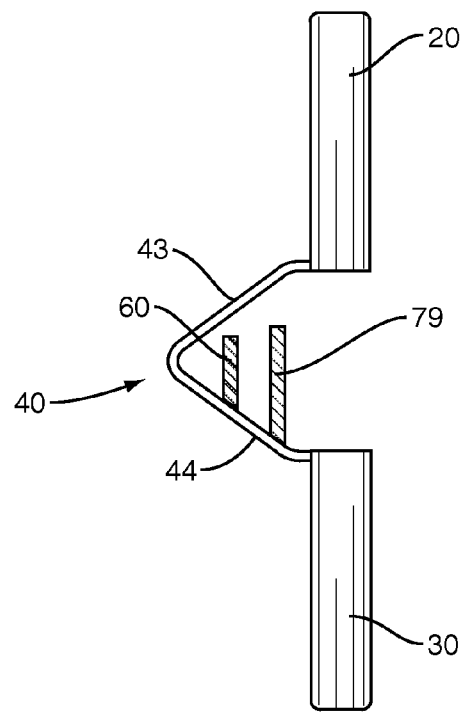
FIG. 14
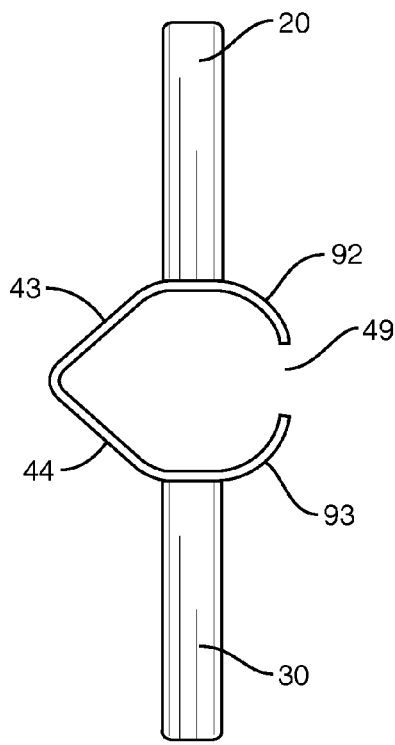 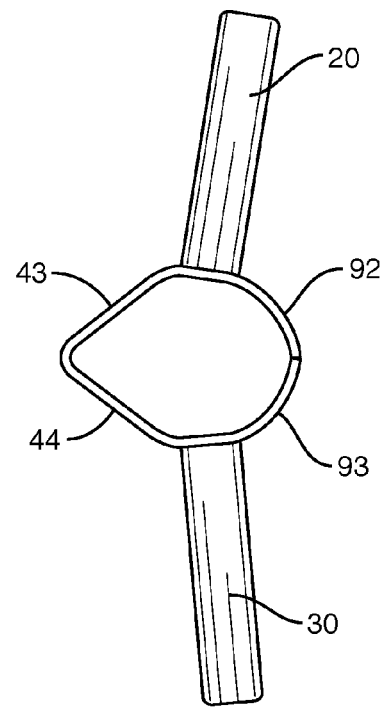
FIG. 15A          FIG. 15B

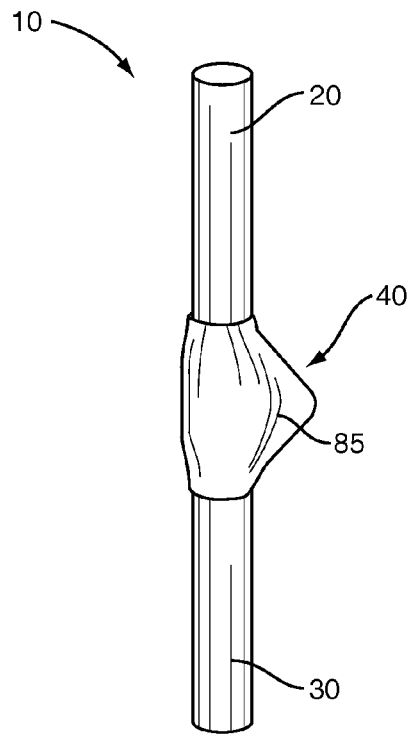 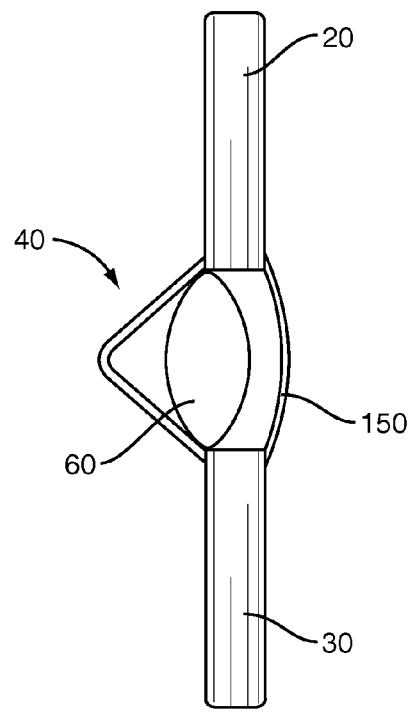
FIG. 16   FIG. 17
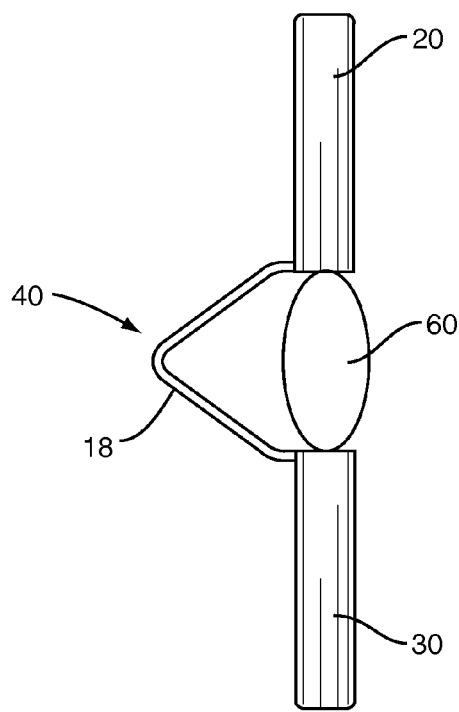
FIG. 18

VERTEBRAL RODS AND METHODS OF USE

RELATED APPLICATION

This application is a division of co-pending application Ser. No. 11/340,973 filed on Jan. 27, 2006 and herein incorporated by reference in its entirety.

BACKGROUND

Vertebral rods are often used in the surgical treatment of spinal disorders such as degenerative disc disease, disc herniations, scoliosis or other curvature abnormalities, and fractures. Different types of surgical treatments are used. In some cases, spinal fusion is indicated to inhibit relative motion between vertebral members. In other cases, dynamic implants are used to preserve motion between vertebral members. For either type of surgical treatment, one or more rods may be attached to the exterior of two or more vertebral members, whether it is at a posterior, anterior, or lateral side of the vertebral members. In other embodiments, rods are attached to the vertebral members without the use of dynamic implants or spinal fusion.

Rods may redirect stresses over a wider area away from a damaged or defective region and restore the spine to its proper alignment. Rods may also increase loading on interbody constructs, decrease stress transfer to adjacent vertebral members while bone-graft healing takes place, and generally support the vertebral members.

SUMMARY

The present application is directed to vertebral rod assemblies. One assembly may include an elongated first rod section and an elongated second rod section spaced from the first rod section. The first and second rod sections may extend along a common centerline. An intermediate section may be attached to and bridge between the rod sections. The intermediate section may have a curved interior surface that faces towards the common centerline. A pocket may be formed between the spaced apart first and second rod sections. The pocket may be bounded on a first side by the intermediate section and may be open along a second side opposite from the intermediate section. An elastic bumper may be disposed in the pocket and formed of a different material than the first and second rod sections and the intermediate section. The elastic bumper may be attached to the intermediate section at multiple locations along a portion of the curved interior surface that is offset from the common centerline. The intermediate section and the elastic bumper may be configured to provide variable resistance to movement of the first and second sections.

The vertebral rod assembly may also include a first rod section and a second rod section spaced from the first rod section. The first and second rod sections may extend along a common centerline. An intermediate section may be attached to and bridge between the rod sections. The intermediate section may have a concave shape with a curved interior surface with a crown located along the curved interior surface that is spaced farthest away from the common centerline. An elastic bumper may be attached to the curved interior surface of the intermediate section and may be configured to provide variable resistance to movement of the first and second rod sections. The elastic bumper may be positioned across the common centerline with a first surface aligned with and facing the crown being on a first side of the common centerline and an opposing second surface facing away from the crown being on an opposing second side of the common centerline. With the rod assembly in a neutral position free from applied loads acting thereon, the first face may include a smaller height measured along the common centerline than the second face.

The vertebral rod assembly may also include an elongated first rod section and an elongated second rod section spaced from the first rod section. The first and second rod sections may extend along a common centerline. An intermediate section may be attached to and bridge between the rod sections. The intermediate section may be offset from the common centerline and have a curved interior surface that faces towards the common centerline. A pocket may be formed by the spaced apart first and second rod sections and the intermediate member. An elastic bumper may be disposed in the pocket and formed of a different material than the first and second rod sections and the intermediate section. The elastic bumper may abut against a majority of the curved interior surface of the intermediate section. The elastic bumper may have a width to extend outward from the curved interior surface across the common centerline. The intermediate section and the elastic bumper may be configured to provide variable resistance to movement of the first and second sections.

BRIEF DESCRIPTION OF THE DRAWINGS

FIG. 11A is a side view illustrating a rod according to one embodiment.

FIG. 11B is a side view illustrating a rod according to one embodiment.

FIG. 12 is a side view illustrating a rod according to one embodiment.

FIG. 13 is a side view illustrating a rod according to one embodiment.

FIG. 14 is a side view illustrating a rod according to one embodiment.

FIG. 15A is a side view illustrating a rod in a first position according to one embodiment.

FIG. 15B is a side view illustrating a rod in a second position according to one embodiment.

FIG. 16 is a side view illustrating a rod and a sleeve according to one embodiment.

FIG. 17 is a side view illustrating a rod according to one embodiment.

FIG. 18 is a side view illustrating a rod according to one embodiment.

DETAILED DESCRIPTION

The present application is directed to vertebral rods and methods of supporting one or more vertebral members. The rod may include upper and lower sections and an intermediate section. An elastic member may be positioned at the intermediate section. The elastic member may have a variety of orientations, sizes, shapes, densities, modulus of elasticity, and other material properties depending upon the desired displacement between the upper and lower sections. The elastic member and/or the intermediate section may be elastically flexible to exert a stabilizing force during movement of the vertebral members.

Figure 1A:
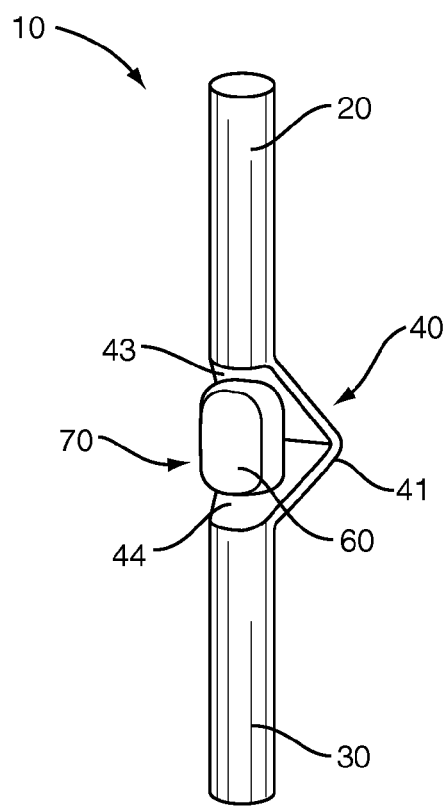
FIG. 1A is a perspective view illustrating a rod according to one embodiment.
Figure 1B:
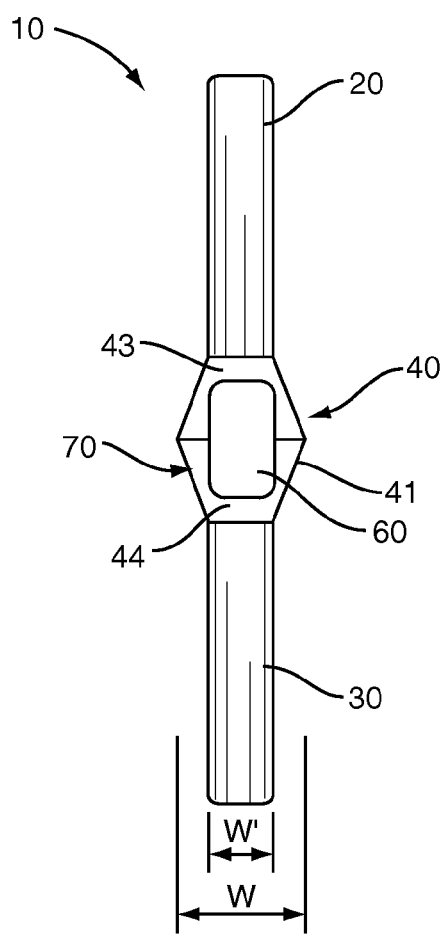
FIG. 1B is a front view illustrating a rod according to one embodiment.

FIG. 1A illustrates a side perspective view and FIG. 1B illustrates a front view of one embodiment of the rod 10. The rod 10 includes an upper section 20 and a lower section 30 separated by an intermediate section 40. An elastic member 60 may be positioned to work in combination with the intermediate section 40 to provide axial and lateral flexibility.

In one embodiment, the intermediate section 40 and elastic member 60 provide variable resistance during movement of the vertebral members 100. The resistance may provide dynamic stabilization during a normal range of motion from the neutral position during flexion, extension, lateral bending, and rotation. The resistance may be caused by placing the intermediate section 40 and elastic member 60 in compression or tension. Further, these elements may switch between compression and tension during movement of the vertebral members. The stiffness of the intermediate section 40 and elastic member 60 may further limit the range of motion beyond a predetermined amount.

Figure 2:
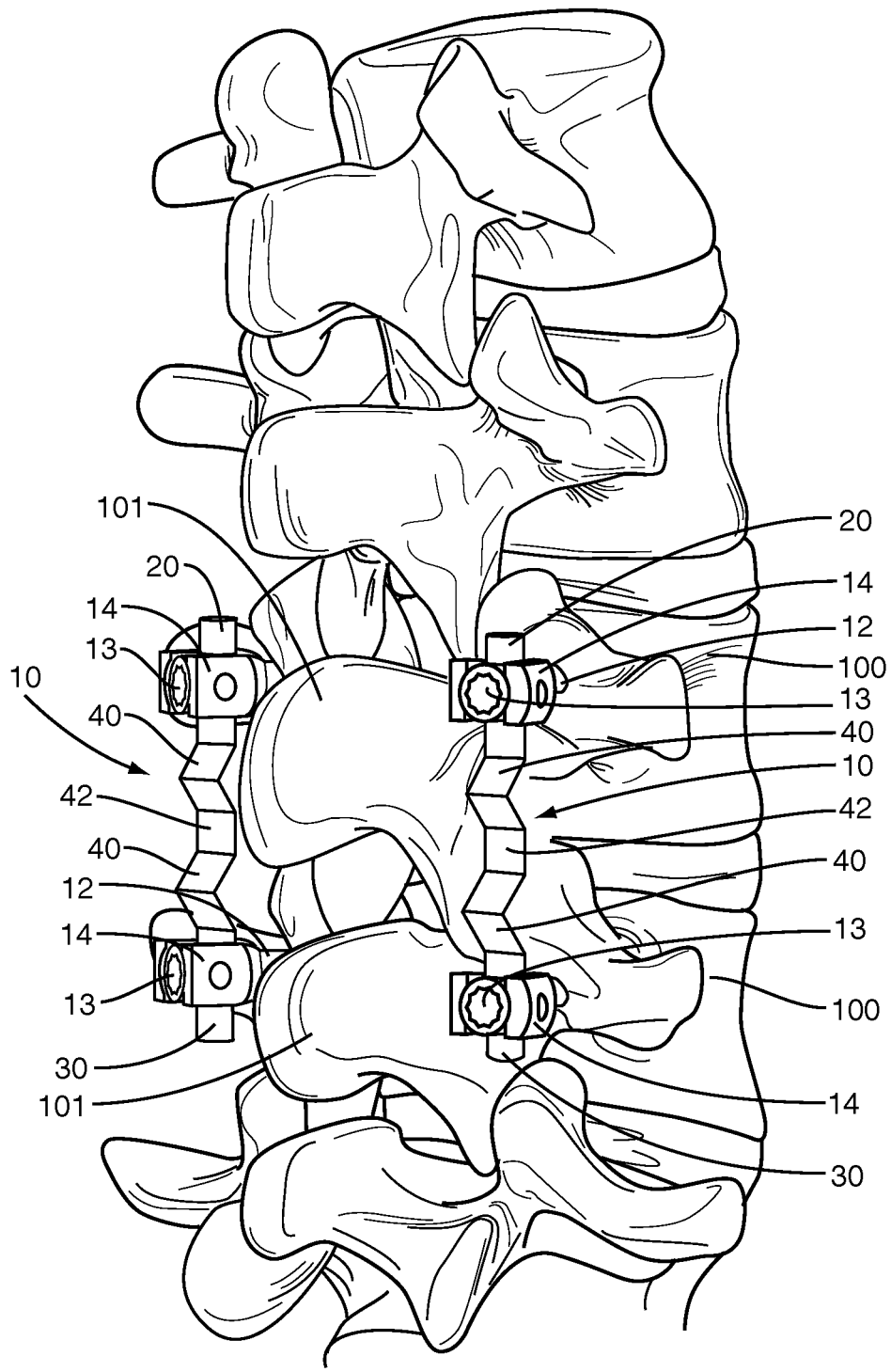
FIG. 2 is a perspective view of a pair of rods attached to vertebral members according to one embodiment.

FIG. 2 illustrates one embodiment of two rods 10 attached to vertebral members 100. In this embodiment, the rods 10 are positioned at a posterior side of the spine, on opposite sides of the spinous processes 101. Rods 10 may be attached to a spine at other locations, including lateral and anterior locations. Rods 10 may also be attached at various sections of the spine, including the base of the skull and to vertebral members 100 in the cervical, thoracic, lumbar, and sacral regions. Thus, the illustration in FIG. 2 is provided merely as a representative example of one embodiment. It is further well understood that a single rod 10 may be used for supporting the vertebral members 100.

In the embodiment of FIG. 2, the rods 10 are secured to the vertebral members 100 by pedicle assemblies comprising a pedicle screw 12 including a receiver 14 and a retaining cap 13. The outer surface of each rod 10 is grasped, clamped, or otherwise secured within the receiver 14 and maintained in position by the retaining cap 13. Other mechanisms for securing rods 10 to the vertebral members 100 include hooks, cables, and other such devices. Further, examples of other types of retaining hardware include threaded caps, screws, and pins. Rods 10 are also attached to plates in other configurations. Thus, the exemplary assemblies shown in FIG. 2 are merely representative of one type of attachment mechanism.

Upper and lower sections 20, 30 may have a variety of shapes, sizes, and physical properties. In one embodiment, the upper and lower sections 20, 30 are substantially identical. In one embodiment, one or both of the sections 20, 30 are substantially cylindrical including an extended length and a circular cross sectional shape. In one embodiment, one or both of the sections 20, 30 are substantially rigid. One or both sections 20, 30 may be substantially straight, include a continuous curve, or include one or more discrete curved sections.

Figure 3:
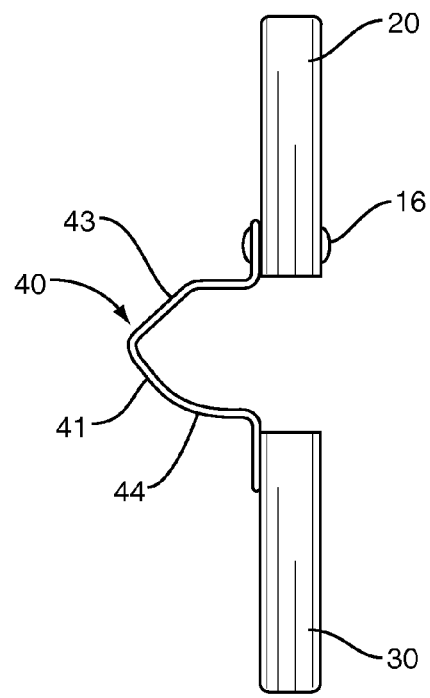
FIG. 3 is a side view illustrating a rod according to one embodiment.

The intermediate section 40 is positioned between the upper and lower sections 20, 30. In one embodiment, the intermediate section 40 and upper and lower sections 20, 30 are constructed of a single piece including a folded or curved configuration. In other embodiments, intermediate section 40 is attached to the upper and lower sections 20, 30. FIG. 3 illustrates one embodiment with the intermediate section 40 constructed of a separate member 41 that is attached to the sections 20, 30. Member 41 is attached to the upper section 20 with one or more fasteners 16. Embodiments of fasteners 16 may include rivets, pins, screws, etc. In the embodiment of FIG. 3, member 41 is attached to the lower section 30 in another manner, such as with adhesives, welding, brazing, etc.

Figure 4:
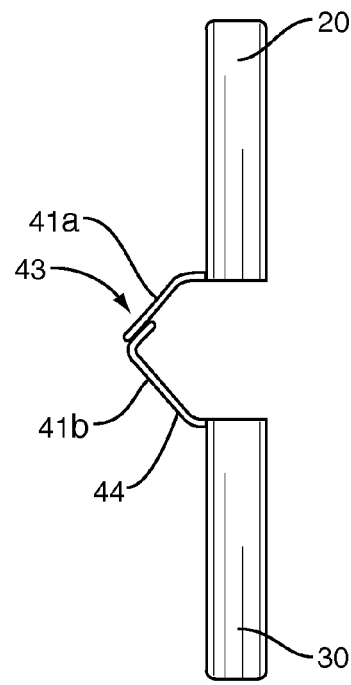
FIG. 4 is a side view illustrating a rod according to one embodiment.

Intermediate section 40 may be constructed from one or more members 41. In the embodiment of FIG. 3, intermediate section 40 is constructed from a single member 41. The embodiment of FIG. 4 illustrates the intermediate section 40 constructed of two separate members 41a, 41b. In this embodiment, first member 41a is connected with section 20, and second member 41b is connected with section 30. Members 41a, 41b are connected together in a manner as described above.

Intermediate section 40 may have a variety of widths. In the embodiment of FIG. 1B, intermediate section 40 has a width w that is greater than a width w' of the upper and lower sections 20, 30. In other embodiments, the width w of the intermediate section 40 is less than or equal to the width w' of the sections 20, 30. In one embodiment, the width w of the intermediate section 40 is up to four times the width of the sections 20, 30. The width w of the intermediate section 40 may vary, as illustrated in the embodiment of FIG. 1B. In another embodiment, the width w is substantially constant.

Figure 6A:
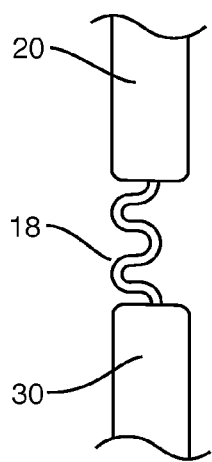
FIGS. 6A-H are side views illustrating a rod according to various embodiment.

Intermediate section 40 may also be positioned at a variety of locations relative to the sections 20, 30. In one embodiment as illustrated in FIG. 3, intermediate section 40 is laterally offset from the sections 20, 30. In another embodiment as illustrated in FIG. 6A, intermediate section 40 is axially aligned with the sections 20, 30.

Figure 5:
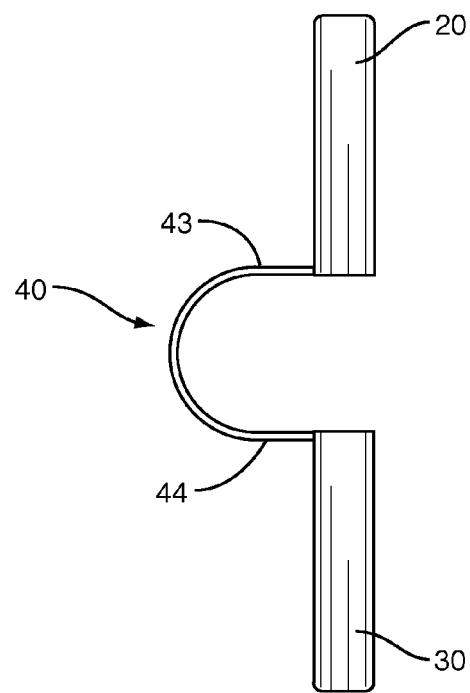
FIG. 5 is a side view illustrating a rod according to one embodiment.

In one embodiment, intermediate section 40 may comprise a member 18 including a first section 43 and a second section 44. First and second sections 43, 44 may comprise the entirety of or a limited portion of the member 18. In one embodiment as illustrated in FIG. 4, intermediate section 40 has substantially planar first and second sections 43, 44. In other embodiments, intermediate section 40 has a curved shape as illustrated in FIG. 5. In various other embodiments such as illustrated in FIG. 3, intermediate section 40 has a combination of planar and curved shapes.

Figure 6B:
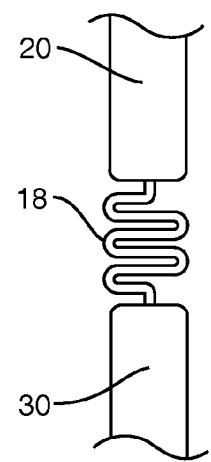
Figure 6C:
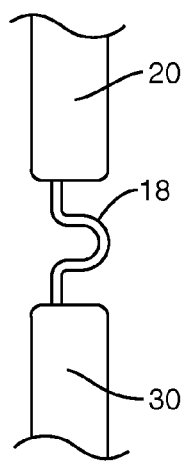
Figure 6D:
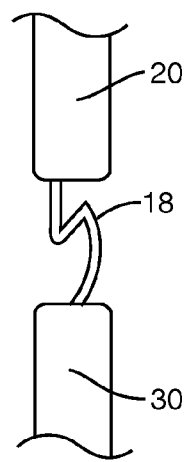
Figure 6E:
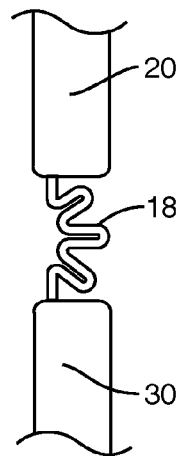

In some embodiments, intermediate section 40 is constructed from a single member 18. FIGS. 6A and 6B illustrate embodiments with the intermediate section 40 comprised of a single member 18 including a curved shape. FIGS. 6C, 6D, and 6E illustrate embodiments having an intermediate section 40 comprised of a single member 18 including planar and curved sections.

Figure 6F:
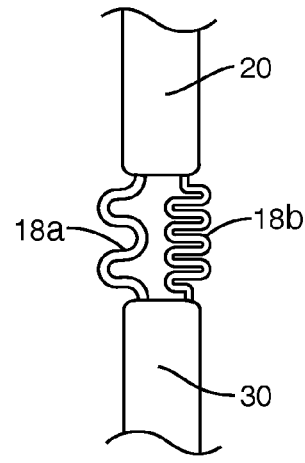
Figure 6G:
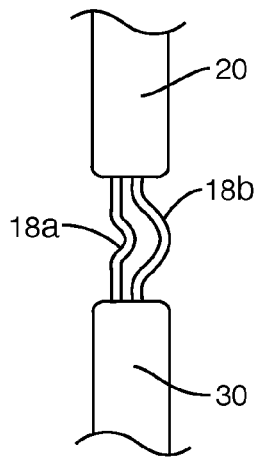
Figure 6H:
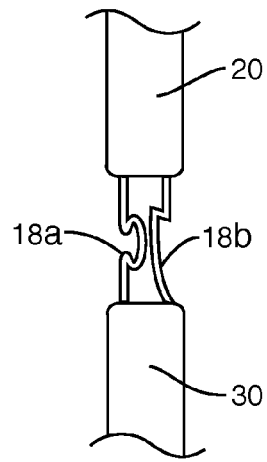

Embodiments of the intermediate section 40 may include multiple members 18. FIG. 6F illustrates an embodiment with a curved first member 18a and a second member 18b. FIGS. 6G and 6H illustrate embodiments with first and second members 18a, 18b each including curved and planar sections. In embodiments having multiple members 18, members 18 may be constructed from a single piece, or multiple different pieces fastened together. Further, the multiple members 18 may be spaced apart, or in close proximity.

Support members 18 may also have an overlapping configuration. The overlap may be in a horizontal direction, vertical direction, or both. Member 18 of FIG. 6A and members 18a and 18b of FIG. 6G illustrate embodiments having vertical overlap with multiple sections of each of these members overlapping vertical between the sections 20, 30. Member 18 of FIGS. 6B, 6C, and 6E also includes vertical overlap. Member 18 of FIG. 6D illustrates an embodiment of horizontal overlap. Horizontal overlap occurs when a line perpendicular to the axis of sections 20 and 30 extends through the member at least twice. Some embodiments feature both horizontal and vertical overlap. Intermediate sections 40 comprising multiple members 18 include horizontal overlap due to the construction. Each of the members 18a, 18b may themselves include horizontal and/or vertical overlap.

In one embodiment as illustrated in FIG. 1A, the intermediate section 40 includes an open side 70. In different embodiments, the open side 70 faces in anterior or posterior directions. In one embodiment, an interior section is formed between the multiple members 18 that comprise the intermediate section 40. The interior section may have two sides enclosed by the members 18. In one embodiment, the lateral sides of the interior section 70 are open. In another embodiment, the interior section 70 is completely enclosed.

Multiple intermediate sections 40 may be positioned along the length of the rod 10. In one embodiment as illustrated in FIG. 2, each rod 10 includes two separate intermediate sections 40. The intermediate sections 40 may include the same or different sizes, shapes, and constructions. A middle section 42 may be positioned along the length of the rod 10 between the intermediate sections 40. In one embodiment, middle section 42 is constructed in a manner as described above for the upper and lower sections 20, 30.

Upper and lower sections 20, 30, and the intermediate section 40 may be constructed of a variety of materials including metals, polymers, ceramics, and combinations thereof. Examples of metals include titanium, titanium alloys such as nickel-titanium, stainless steel, and cobalt chromium. Examples of polymers include silicone, silicone-polyurethane copolymer, polyolefin rubber, PEEK, PEEK-carbon composites, polyimide, polyetherimide, polyurethane, and combinations thereof. Examples of polyurethanes include thermoplastic polyurethanes, aliphatic polyurethanes, segmented polyurethanes, hydrophilic polyurethanes, polyether-urethane, polycarbonate-urethane, silicone polyetherurethane, polyvinyl alcohol hydrogel, polyacrylamide hydrogel, and polyacrylic hydrogel. Examples of ceramics include calcium phosphate, hydroxyapatite, HAPCP, alumina, and zirconium.

The intermediate section 40 may provide resistance to movement of the upper and lower sections 20, 30. Movement of one or both of the sections 20, 30 may cause deformation of the intermediate section 40. In one embodiment, the resistance is substantially constant during movement of the sections 20, 30. In another embodiment, the resistance increases when one or both of the sections 20, 30 move farther away from a first, neutral position. The shape of the intermediate section 40 may also affect the resistance. In one embodiment, relative movement between the sections 20, 30 in a first direction causes a first amount of resistance, and movement in a second, opposite direction causes a second, different amount of resistance. In one embodiment, the differences in resistance may be used to restriction motion of the vertebral members 100 in one direction (e.g., flexion) more than in a second direction (e.g., extension).

An elastic member 60 may be positioned within the intermediate section 40 and has a stiffness to provide resistance to movement of the sections 20, 30. The elastic member 60 may share the load applied to the rod 10 and may prevent fatigue failure of the intermediate section 40. The elastic member 60 may impose a substantially linear or non-linear resistance to resist movement of the sections 20, 30.

Elastic member 60 may be constructed of a variety of different materials. Member 60 may be resilient and change shape during movement of the sections 20, 30. Examples of such materials include elastic or rubbery polymers, hydrogels or other hydrophilic polymers, or composites thereof. Particularly suitable elastomers include silicone, polyurethane, copolymers of silicone and polyurethane, polyolefins, such as polyisobutylene and polyisoprene, neoprene, nitrile, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyetherurethane. Other suitable hydrophilic polymers include polyvinyl alcohol hydrogel, polyacrylamide hydrogel, polyacrylic hydrogel, poly(N-vinyl-2-pyrrolidone hydrogel, polyhydroxyethyl methacrylate hydrogel, and naturally occurring materials such as collagen and polysaccharides, such as hyaluronic acid and cross-linked carboxyl-containing polysaccharides, and combinations thereof.

In one embodiment, elastic member 60 is connected to the intermediate section 40. The elastic member 60 may be connected with mechanical fasteners such as screws, pins, rivets, tethers, sleeves, cables, etc. In another embodiment, elastic member 60 is connected with an adhesive. In one embodiment, the intermediate section 40 includes a roughened surface, ridges, teeth, etc. to maintain the position of the elastic member 60. In one embodiment, the elastic member 60 has a shape that attaches to the intermediate section 40. In a specific embodiment, elastic member 60 includes a dovetail recess that attaches with an extension that extends from the intermediate section 40.

In one embodiment, elastic member 60 is connected to both the first and second sections 43, 44 of the intermediate section 40. When connected to both sections 43, 44, the elastic member 60 provides resistance to both inward and outward movement that may occur during flexion, extension, lateral bending, and rotation. During inward movement of the sections 20, 30, elastic member 60 is compressed and provides a resistance to the inward movement. During outward movement of the sections 20, 30, the elastic member 60 is placed in tension to provide resistance. In one embodiment, the elastic member 60 is placed in compression during extension of the vertebral members and placed in tension during flexion.

In one embodiment with the elastic member 60 connected to one of the first and second sections 43, 44, the elastic member 60 provides resistance to inward movement. However, the elastic member 60 may not be placed in tension during outward movement of the sections 20, 30 and the resistance to this movement is limited to the intermediate section 40.

Figure 7A:
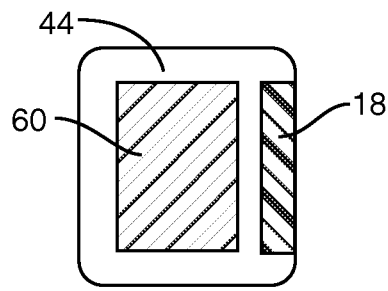
FIGS. 7A-F are cross section views of an elastic member according to various embodiments.
Figure 7B:
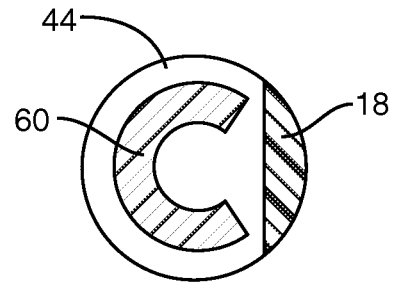
Figure 7C:
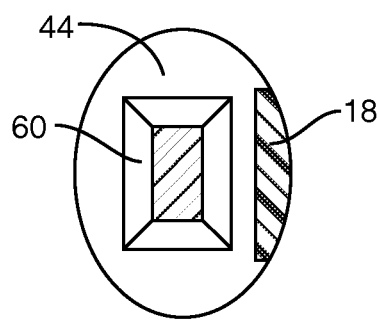
Figure 7D:
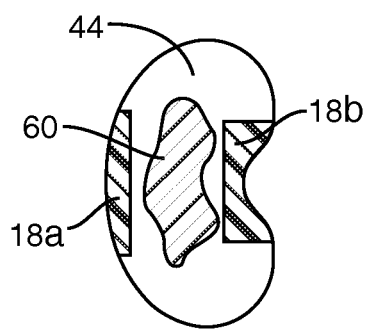

In various embodiments, elastic member 60 is constructed from a single member as illustrated in FIGS. 7A-7D. FIG. 7A illustrates one embodiment having an elastic member 60 with a substantially rectangular shape. FIG. 7B illustrates a substantially C-shaped elastic member 60 with the base facing away from the support member 18. FIG. 7C illustrates an elastic member 60 having a rectangular first surface that contacts the second section 44 and four planar sidewalls that taper upwards. FIG. 7D illustrates an embodiment having an irregular, non-symmetrical shape.

Figure 7E:
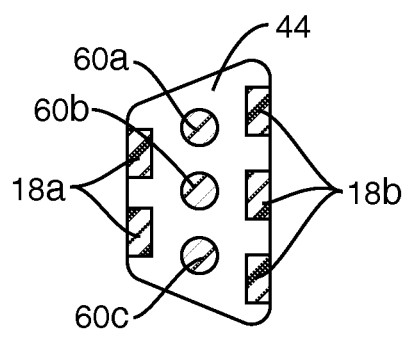
Figure 7F:
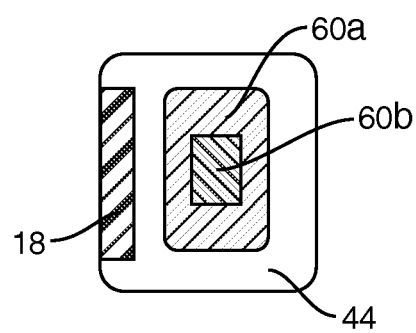

Elastic member 60 may further include two or more separate members. The separate members may have the same construction, or may be constructed of different materials each having a different stiffness. FIG. 7E illustrates an embodiment having three separate elastic members 60a, 60b, 60c. Each elastic member 60a, 60b, 60c is independent and has a substantially circular shape that may be cylindrical, spherical, or conical. FIG. 7F illustrates an embodiment having a first elastic member 60a that extends around a second elastic member 60b. In one embodiment, elastic members 60a, 60b are connected together.

Figure 8:
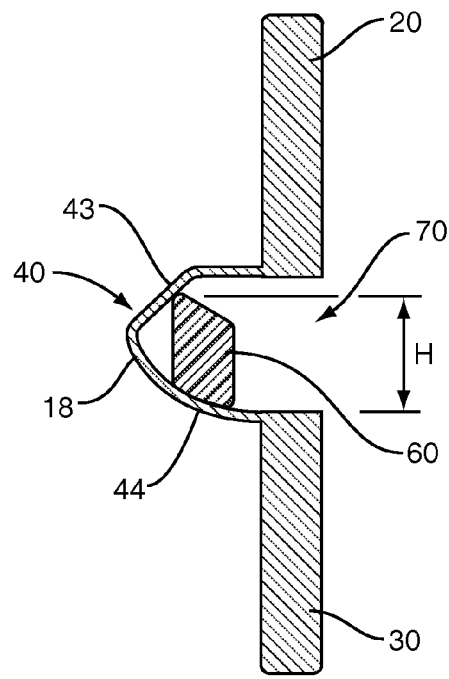
FIG. 8 is a side view illustrating a rod according to one embodiment.
Figure 9:
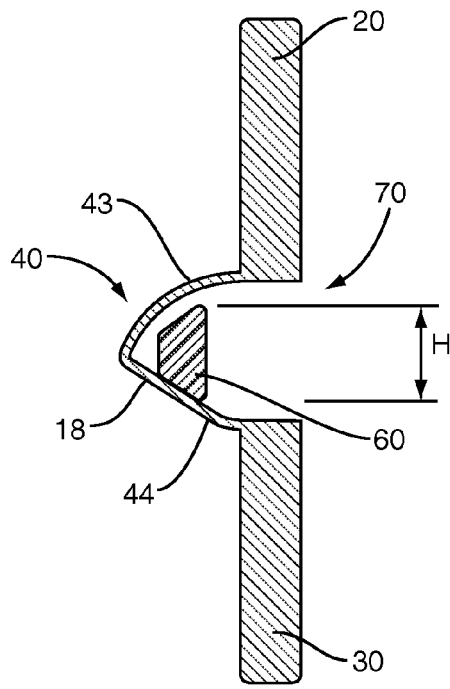
FIG. 9 is a side view illustrating a rod according to one embodiment.

In a neutral condition with no external forces on the rod 10, the elastic member 60 may have a variety of heights H. In one embodiment, the height H is sized for the member 60 to extend between and contact both sections 43, 44. In one embodiment, the height H may be substantially the same throughout the elastic member 60. In other embodiments as illustrated in FIGS. 8 and 9, the height H may vary along the elastic member 60. FIG. 8 includes elastic member 60 having a height H that decreases away from the support member 18, and FIG. 9 includes the elastic member 60 having a height H the increases away from the support member 18.

The device 10 may provide a variable resistance to deformation. The variable resistance may cause less resistance to initial amounts of vertebral movement, but apply greater forces to reduce larger vertebral movements. By way of example, the device 10 may be designed to provide little resistance during an initial amount of movement of the sections 20, 30. Larger amounts of resistance may be applied to the vertebral members when the sections 20, 30 move beyond the initial amount. In some embodiments, the stiffness of the elastic member 60 and intermediate section 40 increases with additional amounts of movement. The amount of resistance applied by each member increases the further they move away from the original, first position.

Variable resistance to inward movement may also result from the height of the elastic member 60. In one embodiment, the height H is less than the height of the opening 70 (i.e., the member 60 does not contact both sections 43, 44). The resistance to the initial movement of the sections 20, 30 is isolated to the intermediate section 40. The elastic member 60 does not affect the stiffness until it is contacted by two sections 43, 44 of the intermediate section 40 and begins to elastically deform. In one embodiment, deformation is limited to the intermediate section 40 during an amount of initial section movement. Movement beyond this initial amount causes the sections 43, 44 to begin deforming the elastic member 60 in addition to continued deformation of the intermediate section 40 resulting in greater stiffness of the device and more resistance to additional movement.

The shape and size of the elastic member 60 may further cause variable resistance to deformation. Greater amounts of contact between the sections 43, 44 and the elastic member 60 may result in greater amounts of resistance. By way of example using the embodiments of FIGS. 8 and 9, the peaked shapes of the elastic members 60 provides less resistance during initial amounts of inward movement of the sections 43, 44. Additional inward movement of the sections 43, 44 results in deformation of larger amounts of the elastic member 60 resulting in greater resistance.

Figure 10:
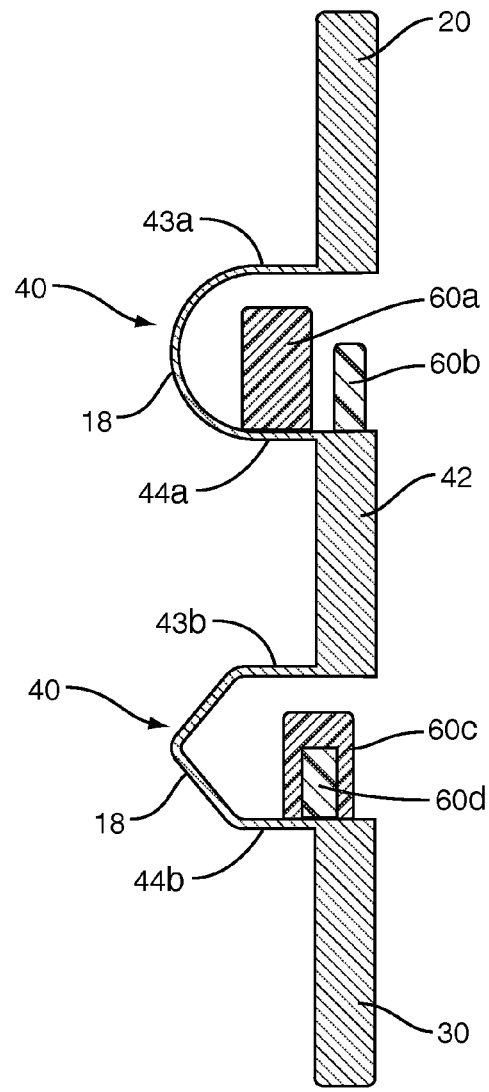
FIG. 10 is a cross section view of a rod according to one embodiment.

Variable resistance may also be provided by multiple elastic elements. FIG. 10 illustrates an embodiment having two intermediate sections 40. A first intermediate section 40 includes two separate elastic members 60a and 60b. During inward movement of the sections 43a, 43b, the inner elastic member 60a is initially contacted thus causing a first amount of resistance. The second elastic member 60b is not contacted by section 43a until the member 60a is compressed beyond a predetermined amount. This compression then causes the elastic member 60b to deform resulting in additional amounts of resistance. The second intermediate 40 section includes a single elastic member constructed of first and second materials 60c, 60d having different stiffnesses. Initial compression of the sections 43b, 44b causes deformation of the first material 60c resulting in a first resistance. Additional compression causes deformation of the first and second materials 60c, 60d which together provide additional resistance.

FIGS. 11A and 11B illustrate another embodiment having first and second members 60a, 60b positioned between the sections 43, 44. As illustrated in FIG. 11A, member 60b has a greater length and is in a slackened configuration when the rod 10 is in a neutral orientation with no external forces. An initial outward movement of the sections 43, 44 is resisted initially by the first member 60a and the intermediate section 40. As the sections 43, 44 move further outward, member 60b is pulled tight. Movement beyond this amount causes the member 60b to be stretched and further movement is opposed by the combination of the first and second members 60a, 60b and the intermediate section 40. Members 60a, 60b may be constructed of the same or different materials.

In one embodiment, member 60b is constructed of an inelastic material and acts as a limiter to control the extent of outward movement. In this embodiment, the sections 43, 44 are moved apart an amount until the member 60b is pulled tight. The inelastic nature of the member 60b then prevents further outward movement of the sections 43, 44 beyond this amount. In one embodiment, member 60b immediately restricts further motion once it is pulled tight, such as occurs with a metallic member. In another embodiment, member 60b provides for a small amount of additional outward movement after being pulled tight prior to stopping further movement. An example includes a woven fabric that expands a slight amount after the member 60b has been pulled tight.

The limiter member 60b as illustrated in the embodiments of FIGS. 11A and 11B may be constructed of a variety of materials including metals, polymers, and ceramics. Examples of metals may include titanium and stainless steel. Examples of polymers may include fibers and textile-based products that are woven or braided. An example of a ceramic is a carbon fiber in a braided configuration.

Elastic member 60 may fill varying amounts of the space between the sections 20, 30. In one embodiment, member 60 fills a limited amount of the intermediate section 40. In another embodiment as illustrated in FIG. 12, elastic member 60 substantially fills the entirety of the interior section 70. In this embodiment, voids 78 are positioned within the elastic member 60. In one embodiment, voids 78 include a specific shape and size to control the supporting abilities of the elastic member 60. Voids 78 may be substantially free of material, or may be filled with a material that is different than that of the elastic member 60. As illustrated in FIG. 12, voids 78 may be positioned within the interior of the elastic member 60, or may be positioned along one edge as illustrated in FIG. 13.

A limiter may prevent movement of the sections 20, 30 beyond a predetermined amount. FIG. 14 illustrates one embodiment having a rigid limiting member 79 positioned within the intermediate section 40 between the sections 43, 44. Movement of one or both sections 20, 30 may cause inward movement of the sections 43, 44 and cause deformation of the elastic member 60. At a predetermined amount of movement, section 43 contacts a top edge of limiting member 79 that prevents further inward movement. Limiting member 79 may have a variety of different shapes and orientations.

Another limiting embodiment is illustrated in FIGS. 15A and 15B. Arms 92, 93 are positioned opposite from sections 43 and 44. Arms 92, 93 include edges that are spaced apart forming a gap 49 in a first position such as in a neutral state as illustrated in FIG. 15A. This allows for a limited amount of inward movement of the sections 43, 44 during vertebral movement. At a predetermined amount of inward movement, edges contact together as illustrated in FIG. 15B and further inward movement is prevented.

In one embodiment as illustrated in FIG. 16, a sleeve 85 extends around the intermediate section 40. In one embodiment, sleeve 85 functions to maintain the elastic material 60 within the intermediate section 40. Sleeve 85 may further provide resistance to movement of the sections 20, 30. In one embodiment, sleeve 85 applies resistance to outward movement of the intermediate section 40. Sleeve 85 may be constructed from materials that are elastic, semi-elastic, or inelastic. Sleeve 85 may be solid, such as constructed from silicone, may be braided or woven, such as a polyester braid or weave, or may be a combination of different materials and constructions.

Tethers 150 may also be used to provide additional resistance to device 10. In one embodiment as illustrated in the embodiments of FIG. 17, tether 150 extends across the open side 70 and is attached to the first and second sections 20, 30. Tether 150 provides resistance during outward movement of the sections 20, 30. In other embodiments, multiple tethers 150 extend across the open side 70. Tethers 150 may have a variety of widths and shapes depending upon the context of use. In one embodiment, tether 150 is constructed of an elastic material that stretches upon movement of the vertebral members 100. In one embodiment, tether 150 is constructed of an inelastic material to prevent movement beyond a predetermined amount. In another embodiment, one or more tethers 150 are connected to the elastic member 60. In one embodiment, the tether 150 is completely contained within the elastic member 60. In one embodiment, tether 150 is positioned completely or in part on the exterior surface of the elastic member 60. In another embodiment, tether 150 extends outward from the elastic member 60. The tether or tethers 150 connected to the elastic member 60 may provide additional resistance during vertebral movement.

FIG. 18 illustrates another embodiment with the elastic member 60 contacting the upper and lower sections 20, 30. In one embodiment, elastic member 60 is spaced away from the member 18. In another embodiment, elastic member 60 is also in contact with the member 18.

When the elastic member 60 is formed from an elastic material, such as a hydrogel, or other similar hydrophilic material, it may deliver desired pharmacological agents. In one embodiment, the pharmacological agents are delivered during deformation of the elastic member 60. The pharmacological agent may be a one used for treating various spinal conditions, including degenerative disc disease, spinal arthritis, spinal infection, spinal tumor and osteoporosis. Such agents include antibiotics, analgesics, anti-inflammatory drugs, including steroids, and combinations thereof. Other such agents are well known to the skilled artisan. These agents are also used in therapeutically effective amounts. Such amounts may be determined by the skilled artisan depending on the specific case.

In one embodiment, the elastic member 60 is attached to the intermediate member 40 to move between positions of tension and compression. During a first motion of the vertebral members 100, the elastic member 60 is placed in compression to provide resistance to the movement. During a second motion of the vertebral members 100, the elastic member 60 is placed in tension to provide resistance to the motion. In one embodiment, the intermediate section 40 is in sequence placed in compression and tension during vertebral movement.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A vertebral rod assembly comprising:
an elongated first rod section;
an elongated second rod section spaced from the first rod section;
the first and second rod sections extending along a common centerline;
an intermediate section attached to each of the rod sections and bridging therebetween, the intermediate section having a curved interior surface that faces towards the common centerline;
a pocket formed between the spaced apart first and second rod sections, the pocket being bounded on a first side by the intermediate section and being open along a second side opposite from the intermediate section;
an elastic bumper disposed in the pocket and formed of a different material than the first and second rod sections and the intermediate section, the elastic bumper attached to the intermediate section at a plurality of locations along a portion of the curved interior surface that is offset from the common centerline;
the intermediate section and the elastic bumper configured to provide variable resistance to movement of the first and second sections.

2. The vertebral rod assembly of claim 1, wherein the elastic bumper is attached to at least one of the first and second rod sections at the common centerline.

3. The vertebral rod assembly of claim 1, wherein each of the first and second rod sections include ends that define a portion of the pocket.

4. The vertebral rod assembly of claim 2, wherein the elastic bumper is attached to the ends of each of the first and second rod sections.

5. The vertebral rod assembly of claim 1, wherein the elastic bumper and the pocket have complementary shapes.

6. The vertebral rod assembly of claim 1, wherein the elastic bumper further includes voids.

7. The vertebral rod assembly of claim 1, wherein a fastener attaches the intermediate section to one of the first and second rod sections.

8. The vertebral rod assembly of claim 1, wherein each of the first and second rod sections are straight.

9. The vertebral rod assembly of claim 1, wherein the intermediate section includes a concave shape with an offset center of curvature disposed between the intermediate section and the common centerline.

10. The vertebral rod assembly of claim 1, wherein the first and second rod sections and the intermediate section have an integral, one-piece construction.

11. A vertebral rod assembly comprising:
a first rod section;
a second rod section spaced from the first rod section;
the first and second rod sections extending along a common centerline;
an intermediate section attached to each of the rod sections and bridging therebetween, the intermediate section having a concave shape with a curved interior surface with a crown located along the curved interior surface that is spaced farthest away from the common centerline;
an elastic bumper attached to the curved interior surface of the intermediate section and configured to provide variable resistance to movement of the first and second rod sections, the elastic bumper positioned across the common centerline with a first surface aligned with and facing the crown being on a first side of the common centerline and an opposing second surface facing away from the crown being on an opposing second side of the common centerline;
with the rod assembly in a neutral position free from applied loads acting thereon, the first face includes a smaller height measured along the common centerline than the second face.

12. The vertebral rod assembly of claim 11, wherein the elastic bumper is attached to the curved interior surface at a plurality of locations.

13. The vertebral rod assembly of claim 12, wherein the elastic bumper is attached to the curved interior surface at the crown.

14. The vertebral rod assembly of claim 11, wherein the crown is equidistant from each of the first rod section and the second rod section.

15. The vertebral rod assembly of claim 11, wherein the crown is located along a section of the curved interior surface that has a constant radius of curvature.

16. The vertebral rod assembly of claim 15, wherein each of the first and second rod sections include ends that face towards each other and form a portion of the pocket.

17. A vertebral rod assembly comprising:
an elongated first rod section;
an elongated second rod section spaced from the first rod section;
the first and second rod sections extending along a common centerline;
an intermediate section attached to each of the rod sections and bridging therebetween, the intermediate section being offset from the common centerline and having a curved interior surface that faces towards the common centerline;
a pocket formed by the spaced apart first and second rod sections and the intermediate member;
an elastic bumper disposed in the pocket and formed of a different material than the first and second rod sections and the intermediate section, the elastic bumper abutting against a majority of the curved interior surface of the intermediate section, the elastic bumper having a width to extend outward from the curved interior surface across the common centerline;
the intermediate section and the elastic bumper configured to provide variable resistance to movement of the first and second sections.

18. The vertebral rod assembly of claim 17, wherein the intermediate section has a concave shape with an offset center of curvature disposed between the intermediate section and the common centerline.

19. The vertebral rod assembly of claim 17, wherein the pocket is bounded on a first side by the intermediate section and being open along a second side opposite from the intermediate section.

20. The vertebral rod assembly of claim 17, wherein the elastic bumper and the pocket have complementary shapes.

* * * * *